United States Patent
Yoon et al.

(10) Patent No.: US 6,991,792 B2
(45) Date of Patent: Jan. 31, 2006

(54) PREVENTION OF AUTOIMMUNE DIABETES BY IMMUNOGENE THERAPY USING RECOMBINANT VACCINIA VIRUS EXPRESSING GLUTAMIC ACID DECARBOXYLASE

(75) Inventors: Ji-Won Yoon, Alberta (CA); Hee-Sook Jun, Chulranam-do (KR)

(73) Assignee: Korea Greencross Corporation, Kyunggi-do (KR)

( * ) Notice: Subject to any disclaimer, the term of this patent is extended or adjusted under 35 U.S.C. 154(b) by 170 days.

(21) Appl. No.: 09/995,829

(22) Filed: Nov. 29, 2001

(65) Prior Publication Data

US 2002/0155596 A1 Oct. 24, 2002

(30) Foreign Application Priority Data

Dec. 29, 2000 (KR) ........................................ 2000-85420

(51) Int. Cl.
*A61K 39/00* (2006.01)

(52) U.S. Cl. ................................ 424/184.1; 424/199.1; 424/204.1; 424/232.1; 424/93.1; 424/93.2; 424/94.1

(58) Field of Classification Search ............... 424/184.1, 424/199.1, 204.1, 232.1, 93.1, 93.2, 94.1
See application file for complete search history.

(56) References Cited

U.S. PATENT DOCUMENTS 5,891,435 A * 4/1999 Muir et al. ............... 424/185.1

OTHER PUBLICATIONS

Couzin Science vol. 300 Jun. 20, 2003 pp. 1862–1865.*
Moss et al. Nucleic Acids Research 1990, 18:4285–4286.*
H.S. Jun, et al. "Prevention of autoimmune diabetes by immunogene therapy using recombinant vaccinia virus expressing glutamic acid decarboxylase." Diabetologia. vol. 45, Apr. 4, 2002. pp. 668–675.
Receipt in the Case of the Original Deposit under the Budapest Treaty on the International Recognition of the Deposit of Microorganisms for the Purposes of Patent Procedure, Nov. 20, 2000.

* cited by examiner

*Primary Examiner*—James Housel
*Assistant Examiner*—Myron G. Hill
(74) *Attorney, Agent, or Firm*—Staas & Halsey LLP

(57) ABSTRACT

A vaccine including recombinant vaccinia virus (ATCC VR-1354) having an inserted gene for coding glutamic acid decarboxylase is used for preventing type 1 diabetes mellitus. The glutamic acid decarboxylase expressed from the recombinant virus suppresses or tolerizes the autoreactive T cell, and induces immunological tolerance, thus effectively prevents or delays the development of type 1 diabetes mellitus.

2 Claims, 12 Drawing Sheets

(7 of 12 Drawing Sheet(s) Filed in Color)

SEQUENCE LISTING

<160> NUMBER OF SEQ ID NOS: 10

<210> SEQ ID NO 1
<211> LENGTH: 20
<212> TYPE: DNA

-continued

```
<213> ORGANISM: Artificial Sequence
<220> FEATURE:
<223> OTHER INFORMATION: IL-2 SENSE

<400> SEQUENCE: 1
cttgcccaag caggccacag                                                   20

<210> SEQ ID NO 2
<211> LENGTH: 20
<212> TYPE: DNA
<213> ORGANISM: Artificial Sequence
<220> FEATURE:
<223> OTHER INFORMATION: IL-2 ANTISENSE

<400> SEQUENCE: 2
gagccttatg tgttgtaagc                                                   20

<210> SEQ ID NO 3
<211> LENGTH: 20
<212> TYPE: DNA
<213> ORGANISM: Artificial Sequence
<220> FEATURE:
<223> OTHER INFORMATION: INF-gamma SENSE

<400> SEQUENCE: 3
agctctgaga caatgaacgc                                                   20

<210> SEQ ID NO 4
<211> LENGTH: 20
<212> TYPE: DNA
<213> ORGANISM: Artificial Sequence
<220> FEATURE:
<223> OTHER INFORMATION: INF-gamma ANTISENSE

<400> SEQUENCE: 4
ggacaatctc ttccccaccc                                                   20

<210> SEQ ID NO 5
<211> LENGTH: 20
<212> TYPE: DNA
<213> ORGANISM: Artificial Sequence
<220> FEATURE:
<223> OTHER INFORMATION: IL-4 SENSE

<400> SEQUENCE: 5
tctttctcga atctaccagg                                                   20

<210> SEQ ID NO 6
<211> LENGTH: 20
<212> TYPE: DNA
<213> ORGANISM: Artificial Sequence
<220> FEATURE:
<223> OTHER INFORMATION: IL-4 ANTISENSE

<400> SEQUENCE: 6
catggtggct cagtactacg                                                   20

<210> SEQ ID NO 7
<211> LENGTH: 21
<212> TYPE: DNA
<213> ORGANISM: Artificial Sequence
<220> FEATURE:
<223> OTHER INFORMATION: IL-10 SENSE

<400> SEQUENCE: 7
caaacaaagg accagctgga c                                                 21
```

```
<210> SEQ ID NO 8
<211> LENGTH: 20
<212> TYPE: DNA
<213> ORGANISM: Artificial Sequence
<220> FEATURE:
<223> OTHER INFORMATION: IL-10 ANTISENSE

<400> SEQUENCE: 8
ttgacctcag cgctgagttg                                              20

<210> SEQ ID NO 9
<211> LENGTH: 23
<212> TYPE: DNA
<213> ORGANISM: Artificial Sequence
<220> FEATURE:
<223> OTHER INFORMATION: SENSE

<400> SEQUENCE: 9
gtaatgatca gtcaacgggg gac                                          23

<210> SEQ ID NO 10
<211> LENGTH: 24
<212> TYPE: DNA
<213> ORGANISM: Artificial Sequence
<220> FEATURE:
<223> OTHER INFORMATION: ANTISENSE

<400> SEQUENCE: 10
caagcaagct tgcaacctta acca                                         24
```

PREVENTION OF AUTOIMMUNE DIABETES BY IMMUNOGENE THERAPY USING RECOMBINANT VACCINIA VIRUS EXPRESSING GLUTAMIC ACID DECARBOXYLASE

BACKGROUND OF THE INVENTION

1. Field of the Invention

The present invention relates to a recombinant vaccinia virus incorporated with a gene coding glutamic acid decarboxylase (hereinafter "GAD") and a vaccine for preventing type 1 diabetes mellitus comprising the same. More particularly, this invention relates to a recombinant vaccinia virus containing a gene coding GAD which is known as pancreatic β cell target autoantigen. The GAD expressed from the recombinant virus suppresses the autoreactive T cell, and induces immunological tolerance, thus effectively prevents or delays the development of type 1 diabetes mellitus.

2. Description of the Related Art

Generally, diabetes mellitus is one of the common metabolic disorders resulting from shortage of insulin, and classified into type 1 diabetes mellitus and type 2 diabetes mellitus according to the effect of insulin injection therapy. Among them, the symptoms of the type 1 diabetes mellitus is relieved by insulin therapy, and the diabetes is generally called as "insulin-dependent diabetes mellitus(IDDM)". The type 1 diabetes mellitus results from the pancreatic β cell destruction due to β cell-specific autoimmunity mediated by the antigen-specific T cells in humans and nonobese diabetic (NOD) mice, and "insulitis" is the major symptom of the disease.

Identification of the primary target β cell antigens in type 1 diabetes mellitus is critical for understanding the initiation of 3 cell-specific autoimmunity by antigen-specific T cells. Many β cell target autoantigens have been identified in humans, nonobese diabetic (NOD) mice and Biobreeding rats, and among these, glutamic acid decarboxylase (GAD) is the strongest candidate in both humans and NOD mice (Tisch, R. et al., Nature 366, 72–75, 1993). In support of this view, we recently found that the β cell-specific suppression of GAD expression results in the prevention of autoimmune diabetes in NOD mice (J. W. Yoon et al., Science 284, 1183–1187, 1999), indicating that GAD expression is essential for the disease induction.

Thus, various methods of suppressing the T cell mediated immune response against pancreatic β cells and thereby inhibiting β cell destruction were developed to prevent or delay insulitis and diabetes. For example, it has been reported that immunization of NOD mice with purified GAD protein (Elliot, J. F., et al., Diabetes 43, 1494–1499,1994) or oral administration of the GAD by feeding with GAD-expressing plants (Ma, S. W., et al., Nature Med. 3. 793–796, 1997) can tolerize the T cell mediated immune response against pancreatic β cells. However, drawbacks to the former method are the difficulty in producing large amount of GAD protein in bacteria due to its insolubility, and the great expense required for the labor-intensive production of large amounts of GAD protein in baculovirus or mammalian cells. Feeding with GAD producing plants also has drawbacks, due to the limited concentration of GAD in the plant and the requirement for long-term feeding.

SUMMARY OF THE INVENTION

In view of the foregoing and to explore the potential of Immunogene therapy based on GAD for the prevention of autoimmune diabetes, we developed a recombinant virus which can express GAD and induce humoral and cell-mediated immune response to a target protein, and found that the induced immune responses are long lived.

Therefore, it is an object of the present invention to provide a recombinant virus for producing relatively large amounts of GAD easily and with low cost. It is other object of the present invention to provide a vaccine for effectively preventing or delaying type 1 diabetes mellitus comprising the recombinant virus, which is safe to human, and free of serious side effect, and induce a strong immune response.

To accomplish these and other advantages, the present invention provides a recombinant vaccinia virus incorporated with a gene for coding glutamic acid decarboxylase. The present invention also provides a vaccine for preventing or delaying type 1 diabetes mellitus comprising the recombinant vaccinia virus.

BRIEF DESCRIPTION OF THE DRAWINGS & PHOTOGRAPHS

The patent or application file contains at least one drawing executed in color. Copies of this patent or patent application publication with color drawings/pictures will be provided by the U.S. Patent and Trademark Office upon request and payment of the necessary fee. A more complete appreciation of the invention, and many of the attendant advantages thereof, will be readily apparent as the same becomes better understood by reference to the following detailed description when considered in conjunction with the accompanying drawings and photographs, wherein.

DETAILED DESCRIPTION OF THE INVENTION

Figure 1:
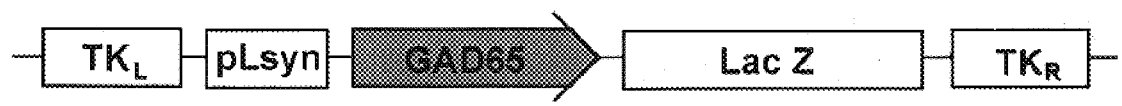
FIG. 1 is a partial schematic structure of GAD-expressing vaccinia virus vector.

For a better understanding of the present invention, reference will now be made in detail to the following disclosures and appended claims.

The recombinant vaccinia virus according to the present invention includes a vaccinia virus as a host cell which is incorporated with a gene for coding glutamic acid decarboxylase(GAD).

The vaccinia virus has been used as a live vaccine against small pox (Fenner, F., Res. Virol. 140, 465–466,1989), and the recombinant vaccinia virus can induce humoral and cell-mediated immune response to a target protein (Hany, M., et al., Eur. J. Immunol. 19, 417–424, 1989) and the induced immune responses are long lived (Moss, B., Science 252, 1662–1667, 1991). It is also known that the virus is safe to human, and it is reported that in phase I clinical trial with vaccinia virus expressing the human immunodeficiency virus I envelope gene, no serious side effects were found in healthy subjects that received percutaneous administration (Cooney, E. L., et al., Lancet 337, 569–572, 1991).

The inserted gene for coding GAD includes nucleotide sequence of GAD65 or its analogous. The amino acid sequence of the GAD and the nucleotide sequence of the murine and human GAD65 are well known in the art (Biochemica et Biophysica Acta 1216, 157–160, 1993, Wo 92/05446). The analogous of nucleotide sequence of GAD65 include partly modified GAD65 having a similar function and a similar structure with GAD65, and being capable of coding protein which still retains biological activity of the native GAD. An example of the modified GAD65 includes GAD65 of which three nucleotides are changed to prevent side effect of gamma-aminobutyric acid (GABA) which is synthesized in the presence of un-modified GAD65 and pyridosal-5'-phosphate (PLP) (Essen et al., WO 95/27051, WO 97/12034). Useful types of nucleotide sequences for cloning and expressing GAD sequences include mRNA, genomic DNA and cDNA, and cDNAs are generally preferred because they lack introns that may interfere with expression.

The gene is cloned into a DNA vector (plasmid vector) such as pMJ601 to produce the recombinant DNA molecule. The recombinant DNA molecule is introduced into vaccinia virus (host cell) according to methods well known to skilled artisan in the art to produce the recombinant vaccinia virus of the present invention. The recombinant vaccinia virus according to the present invention was deposited with the American Type Culture Collection(ATCC), and its ATCC Deposition number is ATCC VR-1354. This deposit was made under the provisions of the Budapest Treaty on the International Recognition of the Deposit of Microorganisms for the Purpose of Patent Procedure and the Regulations thereunder(Budapest Treaty).

The present invention also provides a vaccine for preventing or delaying the type 1 diabetes mellitus comprising the recombinant vaccinia virus as an active ingredient, and pharmaceutically allowable additives. The examples of the pharmaceutically allowable additives includes one or more stabilizer such as fetal serum albumin, lactose, sugar, formalin, gelatin, polysorbate 80, aminoacetic acid, cysteine, ethylenediaminetetra aceticacid, sodium glutamate, and one or more preserving agent such as thimerosal, sulfuric acid Kanamycin, erythromycin, streptomycin, phenol and neomycin. The amount of additives depends on the nature of the additive and the effect to be achieved, and can be easily determined by the skilled artisan in the art.

The vaccine according to the present invention can be injected into patient via non-oral administration methods such as venoclysis, hypodermic injection, and intraperitoneal injection. The amount of the vaccine injected can be varied according to the age, sex, disease of the patient, but the preferable amount is in the range of $1\times10^3 \sim 1\times10^{11}$ PFU, and the more preferable amount is in the range of $1\times10^6 \sim 1\times10^8$ PFU.

The recombinant vaccinia virus (RVV-GAD 65) of the present invention expresses glutamic acid decarboxylase (GAD), and can be used for immunogene therapy of autoimmune diabetes. For example, a single immunization of 3 week-old female NOD mice with RVV-GAD65 almost completely prevented diabetes. In contrast, over 85% of NOD mice given control recombinant vaccinia viruses without the GAD gene developed diabetes within 40 weeks of age. Disease prevention is due to the induction of immunological tolerance, by the active suppression of effector T cells. Therefore, RVV-GAD 65 might have therapeutic value as a potential vaccine for the prevention of type 1 diabetes. The recombinant vaccinia virus expresses β cell autoantigen proteins such as GAD, and can suppress the autoreactive T cell and prevent the development of diabetes. The GAD expressing vaccinia virus according to the present invention has other advantages in that it produces the relatively large amounts of protein easily and with low cost. In addition, the vaccinia virus has another advantages when compared to other vectors or systems. For example, there is a long history of its successful use in humans; it induces a strong immune response and is free of serious side effects. Given these advantages, vaccinia virus expressing GAD may be potentially useful as a vaccine to prevent type 1 diabetes in individuals at high risk for developing the disease.

In order to more fully illustrate the preferred embodiments of the present invention, the following detailed examples are given. In examples, the statistical analyses were carried out using Student's t test.

EXAMPLE 1

Construction of Recombinant Vaccinia Virus Expressing GAD65 Protein (1). The Preparation of Mouse cDNA coding for GAD65

The mouse cDNA coding for GAD65 is prepared by cutting pBlue Script SK integrated with mouse cDNA coding for GAD65 (purchased from Dr. Daniel Kaufman, Univ. of California, Los Angeles) with restriction enzymes XbaI and HindIII. Meanwhile, the vaccinia virus vector pMJ601 (Dr. Ben Moss, NIH) is cut with restriction enzymes NheI and HindIII.

(2). Preparation of Recombinant pMJ-GAD65 Vector

The recombinant pMJ-GAD65 vector was produced by cloning the mouse GAD65 cDNA into NheI and HindIII restriction sites of vaccinia virus vector pMJ601 which has a strong synthetic late promoter. The partial schematic structure of the produced recombinant vector is shown in FIG. 1. As shown in FIG. 1, the recombinant DNA molecule includes a gene coding for Thymidine Kinase left region (TKL), pLsyn, GAD65 cDNA, a gene coding for β-galactosidase(LacZ), and a gene coding for Thymidine Kinase right region (TKR). In FIG. 1, GAD65 represents mouse GAD65 cDNA.

(3). Preparation of RVV-GAD65

A confluent monolayer of CV-1 cells (ATCC, No. CCL-70, Rockville, Md.) which had cultured in DMEM supplemented with 10% FCS(fetal calf serum) and 50 µg/ml gentamycin was infected with 1 ml of wild type vaccinia virus of 0.05 plaque forming unit [PFU]/cell to produce infected cells. The 15 infected cells were placed in $CO_2$ incubator while rocking every 15 minutes for 2 hours. The cell were recovered using scrapers and washed twice with phosphate buffered saline(PBS). The vaccinia virus infected CV-1 cells were electroporated with recombinant plasmid DNAs (20 μg, pMJ-GAD65) using an electroporator (Biorad, Hercules, Calif.) at 0.4 kv, 25 μF. The transfected cell were then incubated for 2 days, and lysed by freezing and thawing. The lysate was used as source of recombinant vaccinia virus for screening.

(4). Screening of RVV-GAD65

HuTK$^-$ 143B cells (ATCC No. CRL8303) was cultured in DMEM including 10% FCS (fetal calf serum), 50 μg/ml of gentamycin and 5 μg/ml of 5-bromodeoxyuridine (BrdU). The cells were seeded at $5 \times 10^5$ cells/well in 6-well tissue culture plate, and cultured until confluence.

The lysates were trypsinized in 0.05% trypsin (Life technologies, Gaithersburg, Md.) for 30 minutes at 30° C., and followed by dilution of the lysate ($10^{-1} \sim 10^{-4}$). The diluted cell lysate were inoculated for 1 hour with rocking every 20 minutes. Before the inoculation was complete, 2% LMP agarose (Life technologies) and 2× MMEM medium (Life technologies) supplemented with 5% FBS, 25 μg/ml of 5-bromodeoxyuridine (BrdU) and 5 μg/ml of gentamycin was warmed in 45° C. water bath. After removal of the viral inoculum from HuTK$^-$ 143B cells, 3 ml of the mixed selective agarose was over-layed and solidified at room temperature. Two day after incubation, 2 ml of agarose mixed with 1 ml of LMP and 1 ml of 2× MMEM containing 100 μg/ml of neutral red(Sigma Chemical Co., St. Louis, Mo.) was over-layed, and the plates were placed overnight at 37° C. The generated plaques were purified separately with sterile cotton-plugged Pasteur pipette, and for the selection of positive recombinant vaccinia virus(RVV-GAD65), several round of plaque purification were performed. The obtained RVV-GAD65 was deposited to ATCC on Nov. 20, 2000 (ATCC No. VR-1354).

EXPERIMENTAL EXAMPLE 1

The Expression of GAD Protein

The expression of GAD protein from the recombinant vaccinia virus obtained in Example 1 was identified by immunohistochemistry of RVV-GAD65-infected cells with GAD specific IgG1 monoclonal antibody (ATCC No. HB184). Briefly, HeLA cells were cultured in Lab-Tek slide flasks (Nunc, Naperville Ill.) and infected with RVV-GAD65. At 3 days after infection, the cells were washed and fixed with acetone. The expressed GAD protein was stained by reacting the GAD protein with the monoclonal antibody, followed by incubation with horseradish peroxidase-conjugated secondary antibody, and visualization using a DAB kit (Vector Laboratory Inc, Burlingame, Calif.). The result is shown in FIG. 2.

COMPARATIVE EXPERIMENTAL EXAMPLE 1

Immunohistochemistry test was carried out according to the same method described in the experimental example 1 except for using the recombinant vaccinia virus RVV-MJ601 (recombinant vaccinia virus containing the vector pMJ601 without the mGAD65 cDNA insert) instead of RVV-GAD65. The result is shown in FIG. 2.

Figure 2:
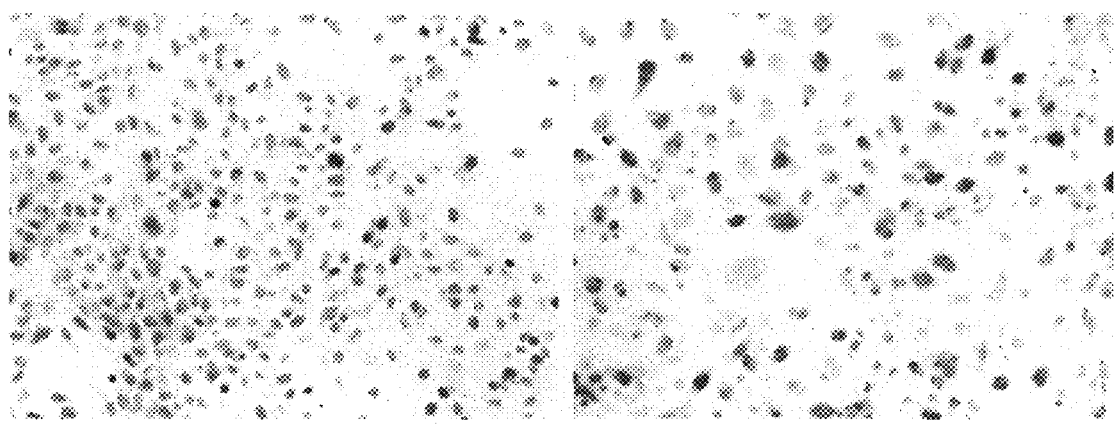
FIG. 2 represents photographs showing immunohistochemical stainings due to GAD expressed in recombinant vaccinia virus of the present invention and recombinant vaccinia virus treated with RVV-MJ601.

In FIG. 2, The left hand side panel represents HeLa cell infected with RVV-MJ601, and the right hand side panel represents HeLa cell infected with RVV-GAD65. As shown in FIG. 2, HeLa cells that has been infected with RVV-GAD65 expressed GAD65 protein, while those infected with RVV-MJ601 (control recombinant vaccinia virus without GAD65 cDNA) did not.

EXPERIMENTAL EXAMPLE 2

The Prevention of the Development of Diabetes (Immunization with Recombinant Vaccinia Viruses)

Figure 3:
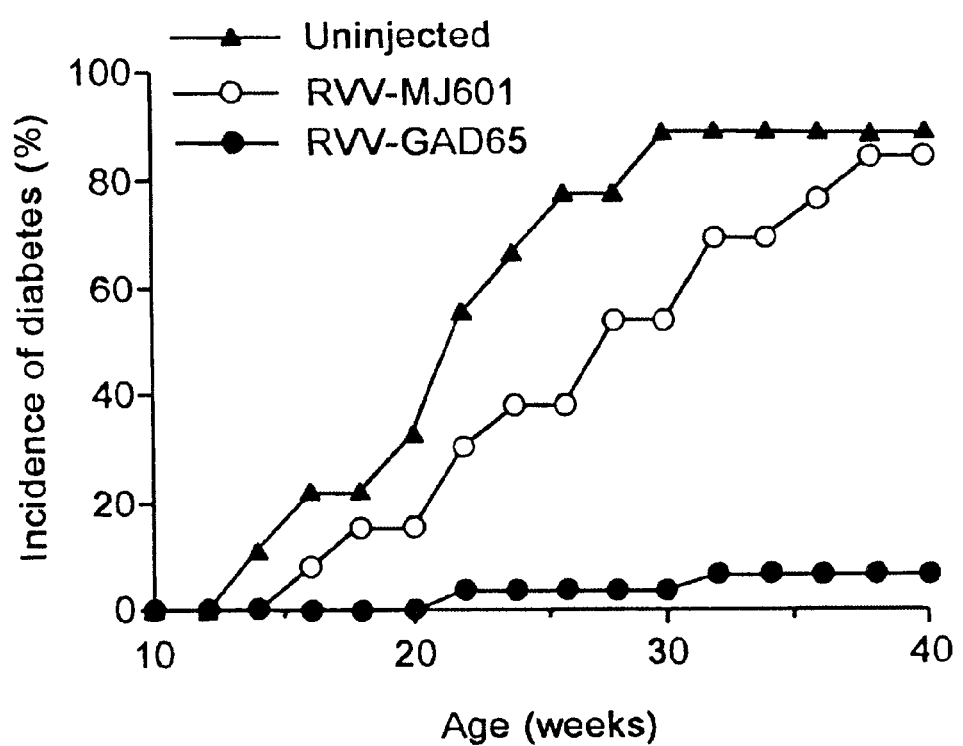
FIG. 3 is a graph showing the development of diabetes of NOD mice treated with RVV-GAD65, RVV-MJ601 and untreated.

Three week-old female NOD mice, obtained from Taconic Co. (Germantown, N.Y.) were intraperitoneally injected with $5 \times 10^7$ PFU of RVV-GAD65. The injected mice were housed under specific pathogen-free conditions. The development of diabetes was monitored by the measurement of urine glucose using Diastix (Miles, ON, Canada) and confirmed by measuring blood glucose using one-touch Basic glucometer (Lifescan, Milpitas, Calif.). Any mouse with a blood glucose level of >16.7 mM on three consecutive days was scored as diabetic. The test results are depicted in FIG. 3

COMPARATIVE EXPERIMENTAL EXAMPLE 2

The development of diabetes was monitored according to the same method described in the experimental example 2 except for using the recombinant vaccinia virus RVV-MJ601 (recombinant vaccinia virus containing the vector pMJ601 without the mGAD65 cDNA insert) instead of RVV-GAD65. The result is shown in FIG. 3.

COMPARATIVE EXPERIMENTAL EXAMPLE 3

The development of diabetes was monitored according to the same method described in the experimental example 2 except for not using the recombinant vaccinia virus. The result is shown in FIG. 3.

As shown in FIG. 3, only seven percent (2/29) of the NOD mice that received RVV-GAD65 developed diabetes, while 85% (11/13) of the NOD mice that received RVV-MJ601 developed diabetes by 40 weeks of age. Similarly, 89% (8/9) of the uninjected control NOD female mice also developed diabetes by the same age. These data suggest that the prevention of diabetes by RVV-5 GAD65 is GAD antigen-specific, and not simply a non-specific effect of the vaccinia virus infection itself. However, the onset of diabetes in the RVV-MJ601 infected mice was somewhat delayed as compared with that in uninjected control NOD mice. The mean age of diabetes onset was 26 weeks in the RVV-MJ601 injected mice as compared to 21 weeks in the uninjected mice.

To determine whether the slight delay in the onset of diabetes in RVV-MJ601 injected NOD mice could be attributed to a non-specific immune disturbance caused by RVV infection, it was examined the cytokine gene expression of splenocytes at different times (1–4 weeks) after infection with the control virus and RVV-MJ601. The expression of interleukin (IL)-2, interferon (IFN)-γ, IL-4 and IL-10 was substantially increased one week after RVV-MJ601 infection as compared to uninfected control virus, thereafter cytokine expression gradually declined, reaching normal levels three weeks after infection. This result suggest that the modest delay in disease onset in RVV-MJ601-injected NOD mice may be due to a non-specific, transient immune disturbance.

Determination of Effective Dose and Age of Administration.

To determine the effective dose and age of administration, 3 week old female NOD mice were intraperitoneally injected with $1 \times 10^7$, $2.5 \times 10^7$ or $5 \times 10^{7\ PFU\ of\ RVV\text{-}GAD}$65, and 8–9 week-old female NOD mice were injected with $5 \times 10^7$ PFU of RVV-GAD65.

The influence of RVV-GAD65 dosage on disease expression was evaluated. The reduction in viral dose had a marked effect. Diabetes occurred in 67% (10/15) of the low dose (1×10⁷ PFU) and 53% (8/15) of the intermediate dose (2.5×10⁷ PFU) groups, as compared to 7% (2/29) in the high dose (5×10⁷ PFU) RVV-GAD65 immunized NOD mice. In addition, the time of RVV-GAD65 immunization altered its effectiveness. When older NOD mice (8 to 9 weeks of age) were immunized with RVV-GAD65 (5×10⁷ PFU/mouse), 73% (8/11) became diabetic, values comparable to those of the unimmunized control NOD mice (75%, 9/12). Thus, the dose of GAD-expressing recombinant vaccinia virus and the age of the NOD mice at the time of immunization determine the effect of the vaccine on the prevention of diabetes.

EXPERIMENTAL EXAMPLE 3

Prevention of Insulitis

Figure 4:
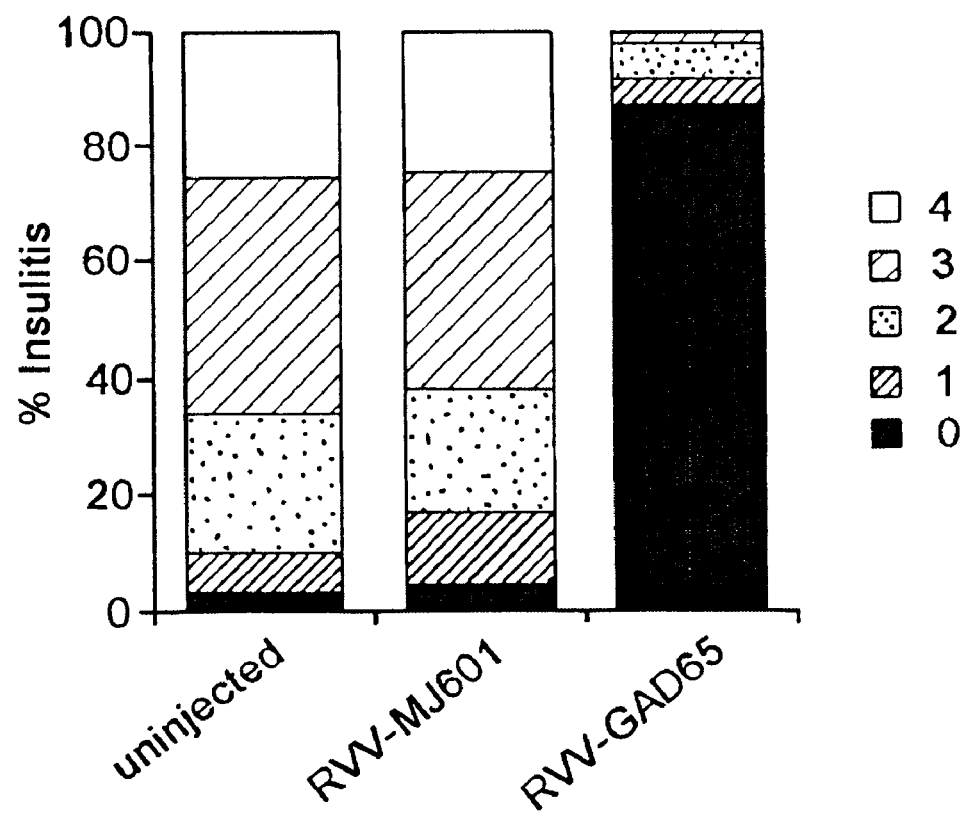
FIG. 4 is a graph showing % insulitis of NOD mice treated with RVV-GAD65, RVV-MJ601 and untreated.
Figure 5A:
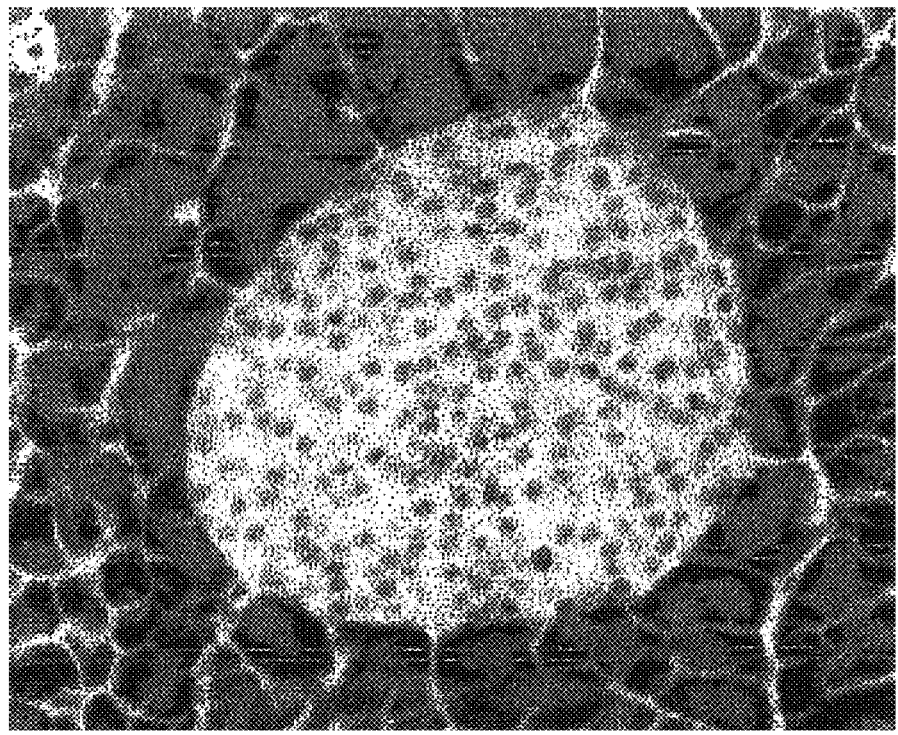
FIGS. 5a–5f are photomicrographs of representative islets and salivary glands from NOD mice treated with RVV-GAD65, RVV-MJ601 and untreated.
Figure 5B:
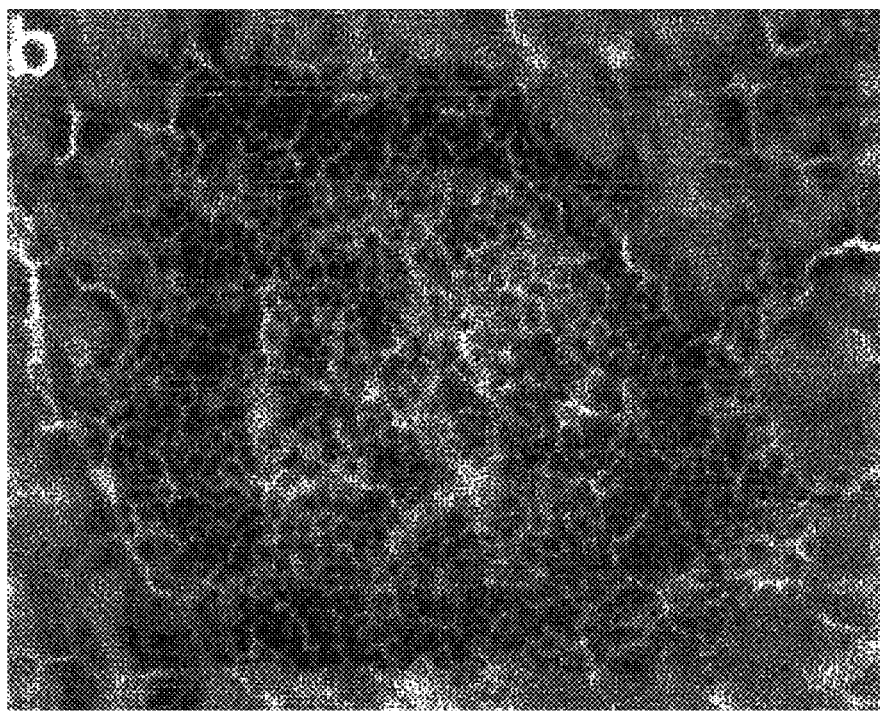
Figure 5C:
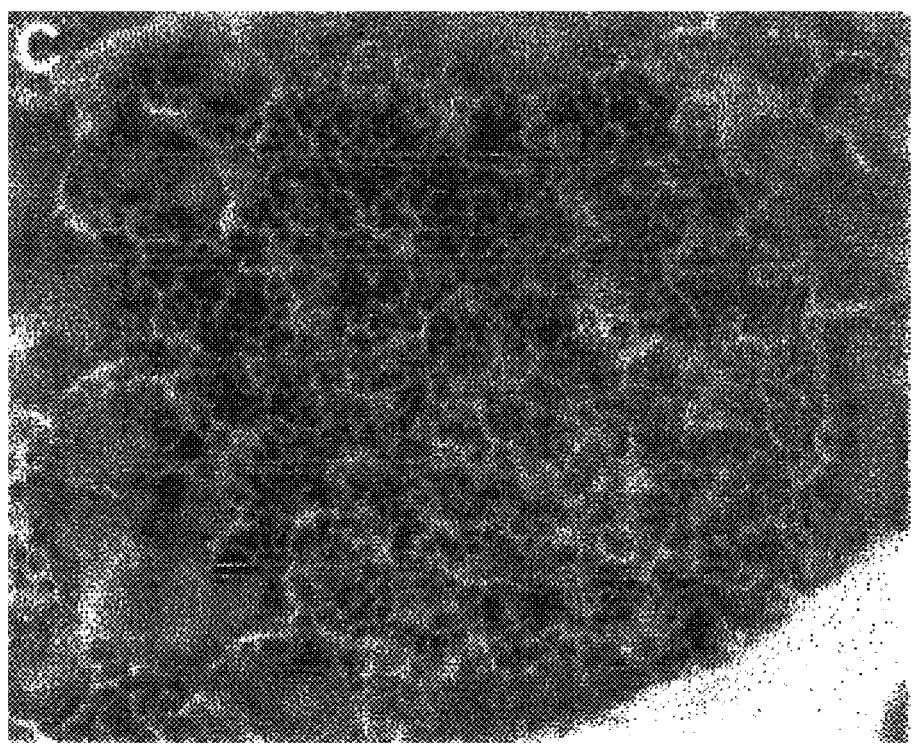
Figure 5D:
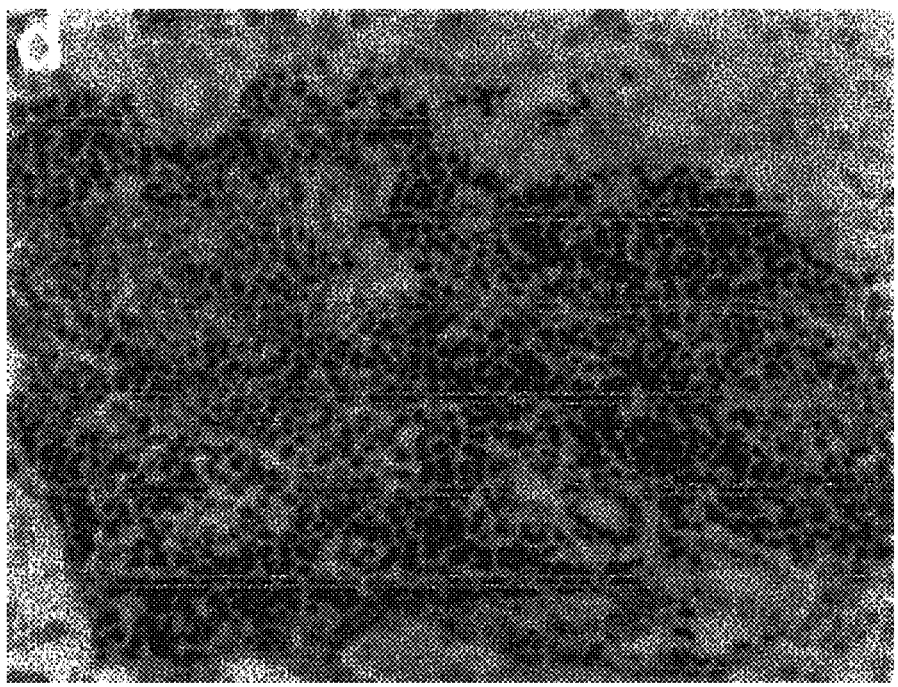

Five mice that have been immunized with RVV-GAD65 (5×10⁷ PFU) at 3 weeks of age were killed at 25 weeks of age and the pancreata (at least 20 islet per mouse) were removed. Each pancreas was fixed with 10% buffered formalin, embedded in paraffin, sectioned at 4.5 cm and stained with hematoxylin and eosin (HE). Insulitis grade was determined as follows, and the results are depicted in FIG. 4. In addition, photomicrographs of representative islets and salivary glands from RVV-GAD65 injected mice are shown in FIGS. 5a and 5d.

0: normal islets

1: mononuclear infiltration, largely in the periphery, in less than 25% of the islets 2: 25% to 50% of islets showing mononuclear infiltration 3: over 50% of islets showing mononuclear infiltration 4: small, retracted islets with few mononuclear cells

COMPARATIVE EXPERIMENTAL EXAMPLE 4

Figure 5E:
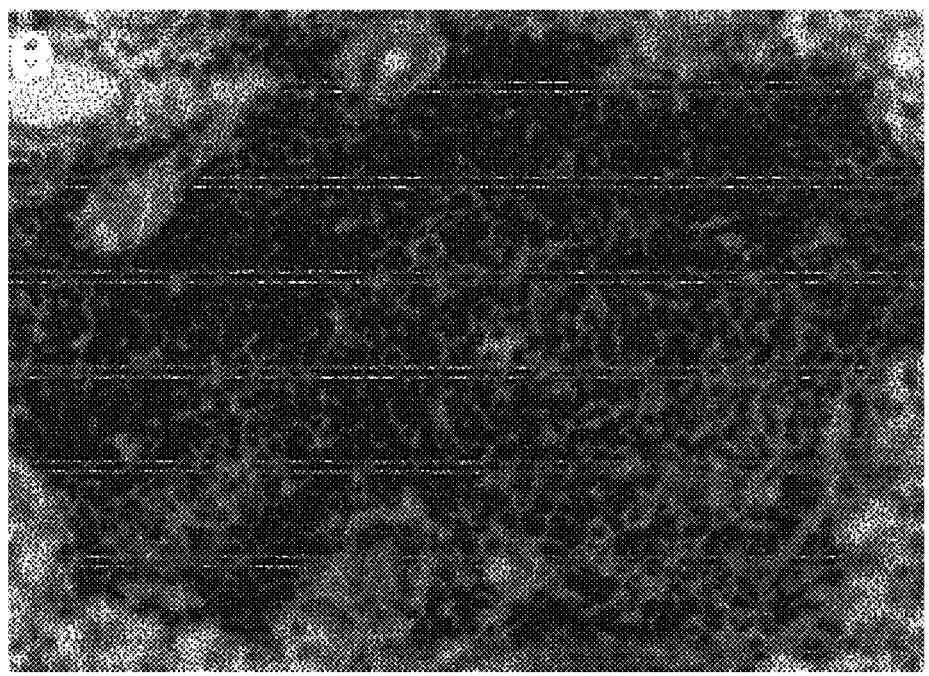

The insulitis grade was determined according to the same method described in the experimental example 3 except for using mice that has been immunized with RVV-MJ601. The result is shown in FIG. 4. In addition, photomicrographs of representative islets and salivary glands from RVV-MJ601 injected mice are shown in FIGS. 5b and 5e.

COMPARATIVE EXPERIMENTAL EXAMPLE 5

Figure 5F:
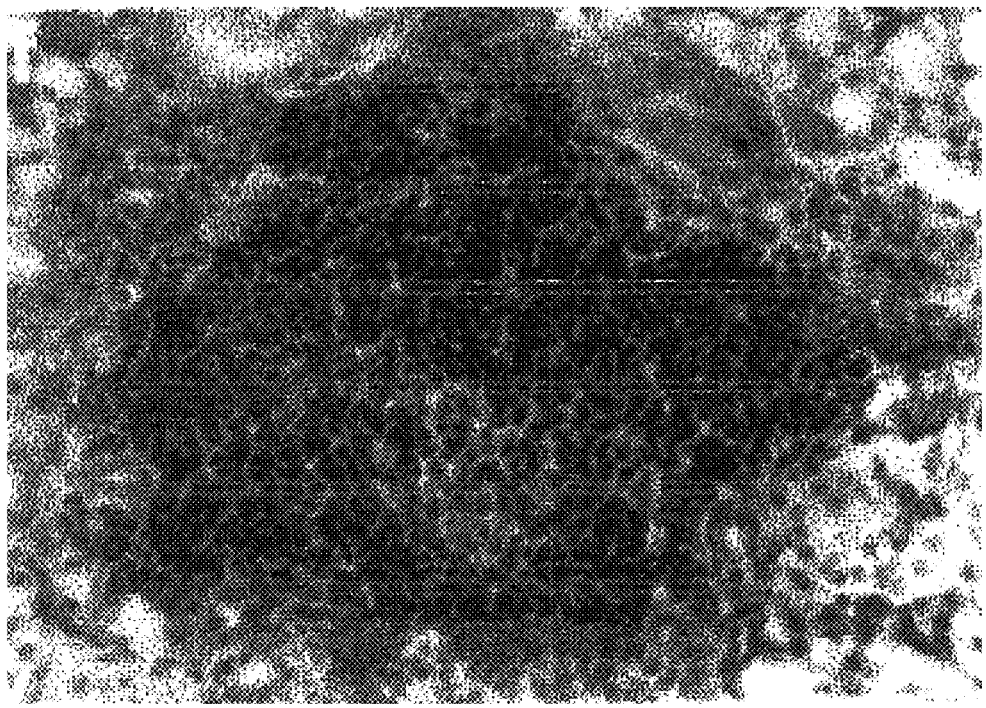

The insulitis grade was determined according to the same method described in the experimental example 3 except for using uninjected mice. The result is shown in FIG. 4. In addition, photomicrographs of representative islets and salivary glands from the RVV non-injected mice are shown in FIGS. 5c and 5f.

As shown in FIG. 4, the development of insulitis in NOD mice infected with RVV-GAD65 was significantly reduced as compared to those infected with RVV-MJ601. Eighty-seven percent of the examined islets from RVV-GAD65 injected NOD mice were intact (See FIG. 4 and FIG. 5a), whereas 83% of the islets from RVV-MJ601 injected NOD mice showed moderate to severe insulitis, similar to that found in uninjected control NOD mice, at 25 weeks of age (FIG. 4 and FIGS. 5b and 5c). At 40 weeks of age, when the experiment was terminated, 42% of the examined islets from RVV-GAD65 injected mice remained intact, 50% of the islets showed mild peri-insulitis or moderate insulitis, and only about 8% of the islets showed severe insulitis.

To determine whether the immunization of NOD mice with RVV-GAD65 specifically effect β cell-specific autoimmunity, the salivary glands which show lymphocytic infiltration in NOD mice was examined. There was equally severe infiltration of lymphocytes in the salivary glands of both RVV-GAD65 and RVV-MJ601 infected NOD mice at 25 weeks of age (FIGS. 5d and 5e), similar to that of uninjected NOD mice (FIG. 5f). These results indicate that the suppression of autoimmunity induced by immunization with RVV-GAD 65 encompass only the pancreatic islets, and not other target tissues that do not express GAD protein.

EXPERIMENTAL EXAMPLE 4

Toleration of T Cells to GAD

Figure 6:
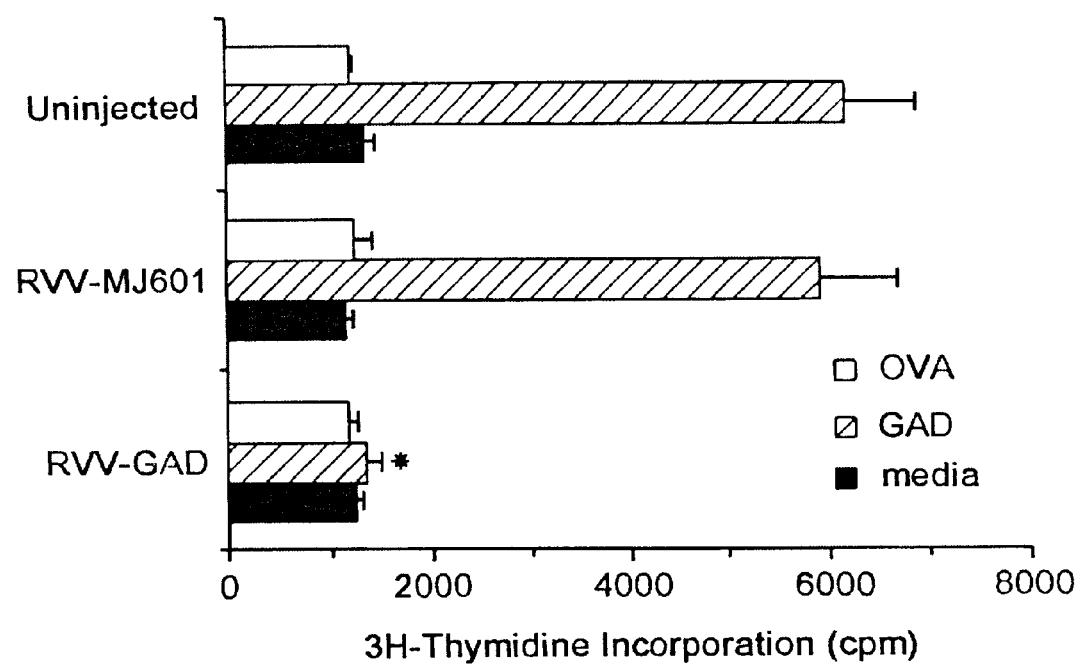
FIG. 6 is a graph for illustrating the proliferative response of splenocytes isolated from NOD mice treated with RVV-GAD65, RVV-MJ601 and untreated.

To determine the diabetes preventing mechanism by RVV-GAD65, the proliferative response to GAD protein of splenocytes of mice was examined. Single cell splenocytes were prepared from NOD mice 8 weeks after injection of RVV-GAD65. The cells (5×10⁵) were cultured in 200 μl of complete RPMI-1640 medium supplemented with 10% fetal bovine serum, 1 mM L-glutamine, 100 U/ml penicillin, 100 μg/ml streptomycin and 50 μM β-mercaptoethanol in a 96-well microplate in the presence of GAD protein produced in baculovirus for 72 hr. The cells were then pulsed with ³H-tymidine (1 μCi/well) for 16 to 18 hr. The proliferation was quantified by determining the ³H-tymidine incorporation using a liquid scintillation counter. The result is shown in FIG. 6. In FIG. 6, results are shown as cpm±SD of three experiments using 2 mice per group.

COMPARATIVE EXPERIMENTAL EXAMPLE 6

The proliferation was determined according to the same method described in the experimental example 4 except for using mice that has been immunized with RVV-MJ601. The result is shown in FIG. 6.

COMPARATIVE EXPERIMENTAL EXAMPLE 7

The proliferation was determined according to the same method described in the experimental example 4 except for using age- and sex-matched uninjected NOD mice. The result is shown in FIG. 6.

As shown in FIG. 6, these splenocytes collected 8 weeks after injection with RVV-GAD65 did not respond to GAD. In contrast, GAD stimulated the proliferation of the splenocytes collected from RVV-MJ601 injected mice and uninjected control NOD mice. Splenocytes from all three groups showed no proliferative response against ovalbumin, an antigen unrelated to β cell proteins. These results imply that GAD-reactive T cells are tolerated in RVV-GAD65 injected animals.

EXPERIMENTAL EXAMPLE 5

Humoral Immune Response Against GAD

Figure 7:
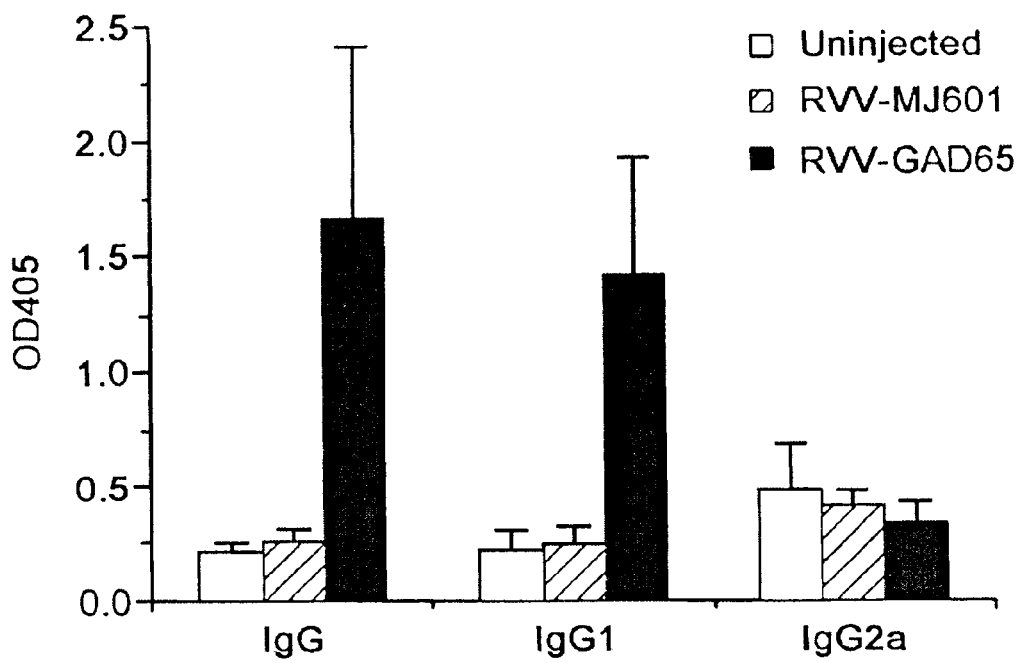
FIG. 7 is a graph for illustrating the humoral immune response of NOD mice treated with RVV-GAD65, RVV-MJ601 and untreated.

Sera from NOD mice was collected 8 weeks after injection with RVV-GAD65, and reacted with GAD65 protein produced in baculovirus according to the method provided by Elliot et al (J. F. Elliot et al., Diabetes 43, 1494–1499, 1994). GAD65 protein was dissolved in 0.1M NaHCO₃, pH 8.5 (10 μg/ml of GAD65 in 0.1 M NaHCO₃, pH 8.5), and coated onto a 96-well microplate at 4° C. overnight. After washing the microplate, the bound antibody was reacted with alkaline phose-conjugated goat anti-mouse IgG, anti-mouse IgG1 or anti-mouse IgG2a antibodies. The color was developed by incubation with 4-nitrophenylphosphate. The optical density was read at 405 nm by ELISA reader to determine the level of antibodies to GAD. The result is shown in FIG. 7. In FIG. 7, values are shown as mean±SD of 7 mice.

COMPARATIVE EXPERIMENTAL EXAMPLE 8

The level of antibodies to GAD was determined according to the same method described in the experimental example 5 except for using sera of RVV-MJ601 injected mice. The result is shown in FIG. 7.

COMPARATIVE EXPERIMENTAL EXAMPLE 9

The level of antibodies to GAD was determined according to the same method described in the experimental example 5 except for using sera of uninjected, and age- and sex-matched mice. The result is shown in FIG. 7.

As shown in FIG. 7, there was an increase in the level of IgG antibodies to GAD in the serum of RVV-GAD 65 injected mice as compared to RVV-MJ601 injected and uninjected mice. When the isotype of the IgG antibodies to GAD were examined, the level of the IgG1 subtype was specifically increased in RVV-GAD65 immunized NOD mice, whereas the IgG2 subtype was unchanged, as compared to RVV-MJ601 injected NOD mice. These observations suggest that the recombinant virus enhanced the Th2 immune response.

EXPERIMENTAL EXAMPLE 6

Cytokine Production

Figure 8:
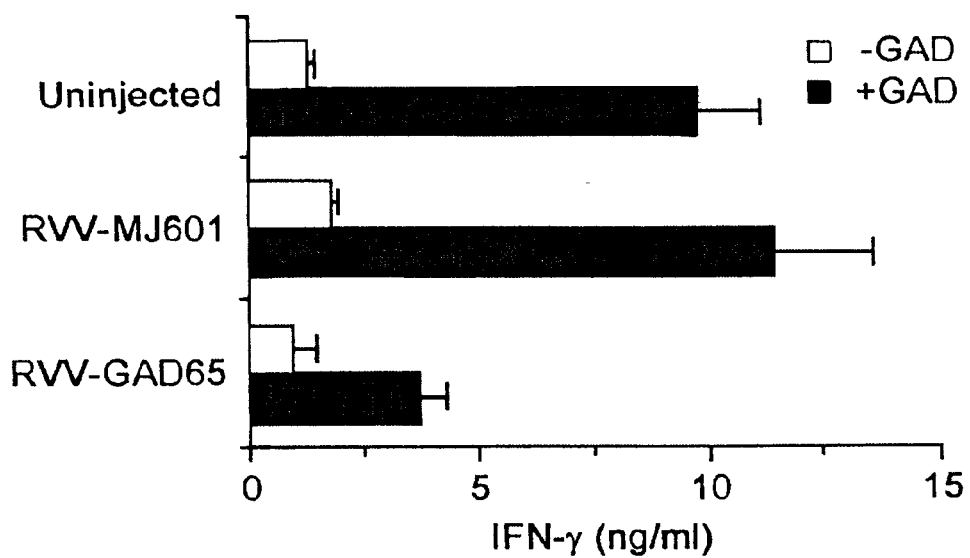
FIG. 8 is a graph showing the production of IFN-γ in the splenic T cell of mice treated with RVV-GAD65, RVV-MJ601 and untreated.
Figure 9:
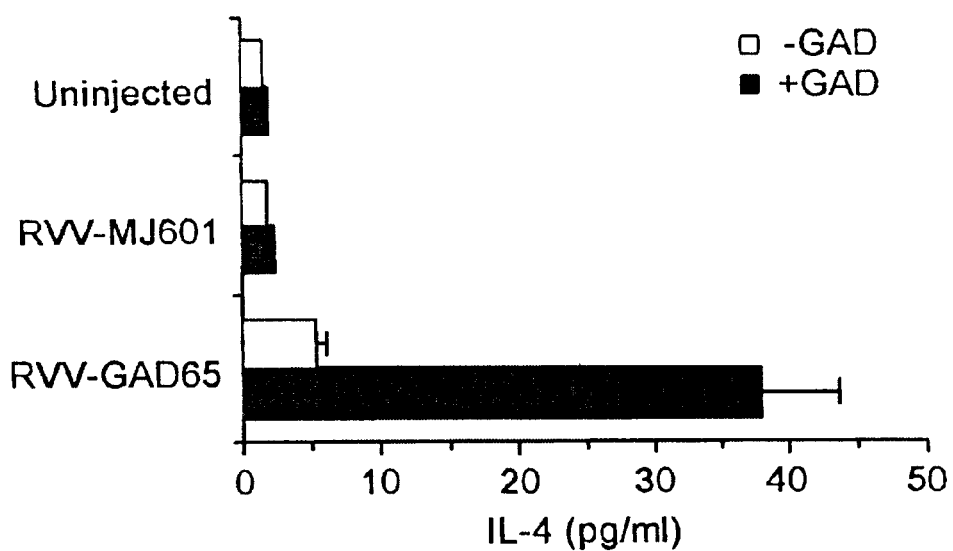
FIG. 9 is a graph showing the production of IL-4 in the splenic T cell of mice treated with RVV-GAD65, RVV-MJ601 and untreated.

The production of cytokines in the splenic T cells of RVV-injected NOD mice was measured as described previously (H. S. Jun et al., J. Exp. Med. 189, 347–358, 1999). Splenocytes were isolated 8 weeks after injection of RVV-GAD65. The cells were cultured in 24-well plates ($1 \times 10^6$ ells/well) in complete RPMI-1640 medium in the presence of GAD protein or ovalbumin for 72 hr. The supernatant was collected and IFN-γ and IL-4 production was measured by sandwich ELISA using a Quantikine kit (R&D systems, Minneapolis, Minn.). The results are shown in FIGS. 8 and 9, respectively.

COMPARATIVE EXPERIMENTAL EXAMPLE 10

IFN-γ and IL-4 production in the splenic T cells was measured according to the same method described in the experimental example 6 except for using RVV-MJ601 injected mice. The results are shown in FIGS. 8 and 9, respectively.

COMPARATIVE EXPERIMENTAL EXAMPLE 11

IFN-γ and IL-4 production in the splenic T cells was measured 19 according to the same method described in the experimental example 6 except for using uninjected mice. The results are shown in FIGS. 8 and 9, respectively.

Figure 10:
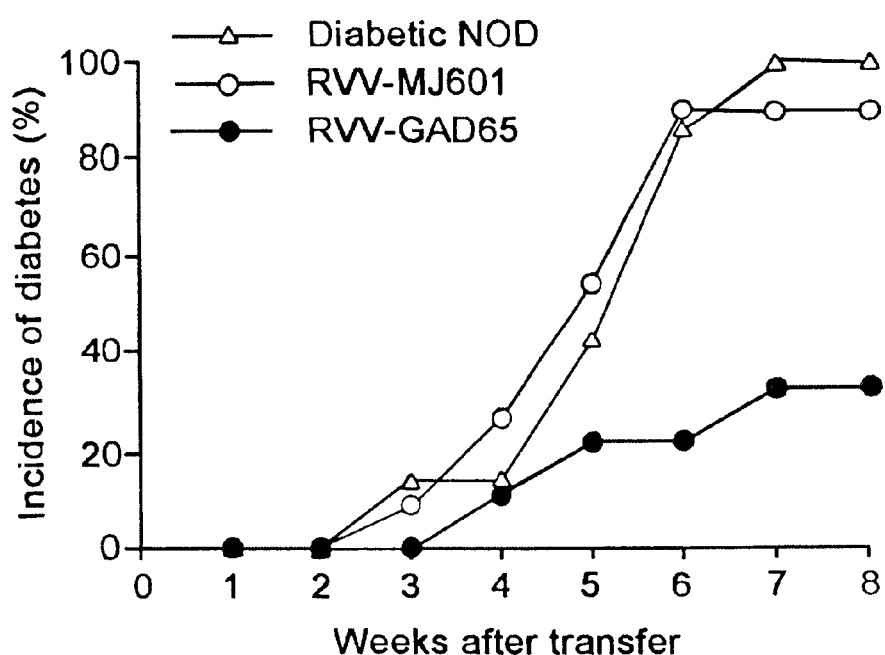
FIG. 10 is a graph showing the adoptive transfer of diabetes in mice treated with RVV-GAD65, RVV-MJ601 and untreated.

As shown in FIGS. 9 and 10, the production of IL-4 was increased, 5 whereas the production of IFN-γ was decreased in the splenocytes of RVV-GAD65 injected mice as compared to splenocytes from RVV-MJ601 injected NOD mice. These results suggest that immunization of NOD mice with RVV-GAD65 induces a Th2 immune response in an antigen-specific manner.

EXPERIMENTAL EXAMPLE 7

Reverse Transcriptase Polymerase Chain Reaction (RT-PCR) Analysis

Total RNA was isolated from splenocytes of RVV-GAD65 immunized mice at 1, 2 and 3 weeks after immunization using a RNA extraction kit (Qiagen Inc, Mississauga, ON, Canada) according to the manufacturer's protocol. Two jig of total RNA was converted to cDNA using Superscript II reverse transcriptase (Gibco BRL, Gaithersburg, Md.) and oligo (dT). PCR was performed using specific primers for various cytokine genes(H. S. Jun et al., J. Exp. Med. 189, 347–358, 1999). The primers used were as follows:

```
IL-2:   sense-      CTTGCCCAAGCAGGCCACAG      (SEQ ID NO:1)
        Antisense-  GAGCCTTATGTGTTGTAAGC      (SEQ ID NO:2)
IFN-γ   sense-      AGCTCTGAGACAATGAACGC      (SEQ ID NO:3)
        Antisense-  GGACAATCTCTTCCCCACCC      (SEQ ID NO:4)
IL-4:   sense-      TCTTTCTCGAATCTACCAGG      (SEQ ID NO:5)
        Antisense-  CATGGTGGCTCAGTACTACG      (SEQ ID NO:6)
IL-10:  sense-      CAAACAAAGGACCAGCTGGAC     (SEQ ID NO:7)
        Antisense-  TTGACCTCAGCGCTGAGTTG      (SEQ ID NO:8)
```

Hypoxanthine phosophoribosyl tranferase(HPRT) mRNA was amplified as an internal standard, the primers used for HPRT were as follows.

```
Sense-      GTAATGATCAGTCAACGGGGAC       (SEQ ID NO:9)
Antisense-  CAAGCAAGCTTGCAACCTTAACCA     (SEQ ID NO:10)
```

The PCR conditions were optimized for each set of primers. PCR was performed using different numbers of cycles to ensure that amplification occurred in a linear range. The PCR mixture (50 µl) contained 0.2 mM of deoxynucleotide triphosphate, 1 µM of each specific primer, 1.5 mM or 2 mM $MgCl_2$, 50 mM KCl, 10 mM Tris-Cl (pH 9.0) and 2.5 units of Taq polymerase (Pharmacia Biotech, Uppsala, Sweden). After amplification, the products were subjected to electrophoresis on a 1.5% agarose gel, and detected by ethidium Bromide staining.

EXPERIMENTAL EXAMPLE 8

Adoptive Transfer of Diabetes

This experimental example is to examine whether immunization of NOD mice with GAD65 might promote the generation of a regulatory immune response, resulting in the protection of β cells destruction by effector T cells. Firstly, three week-old female NOD mice were injected with RVV-GAD65 ($5 \times 10^7$ PFU/mouse). Then, at 20 weeks of age, spienocytes ($1 \times 10^7$ cells) were isolated from each donor and injected i.p. with the splenocytes ($1 \times 10^7$ cells) from uninjected, acutely diabetic NOD mice into 6 to 8 week old NOD scid mice. The development of diabetes was determined by the measurement of urine and blood glucose every other day. The result is shown in FIG. 10.

COMPARATIVE EXPERIMENTAL EXAMPLE 12

The measurement of urine and blood glucose (the development of diabetes) were measured according to the same method described in the experimental example 8 except for using RVV-MJ601 injected NOD mice. The result is shown in FIG. 10.

COMPARATIVE EXPERIMENTAL EXAMPLE 13

The measurement of urine and blood glucose (the development of diabetes) were measured according to the same method described in the experimental example 8 except for using non-injected NOD mice. The result is shown in FIG. 10.

As shown in FIG. 11, 33% (3 out of 9) of the NOD scid recipients of splenic lymphocytes that included cells from RVV-GAD 65 injected NOD mice developed diabetes, whereas 90% (9/10) of the NOD scid recipients of splenic lymphocytes that included cells from RVV-MJ601 injected mice developed diabetes. These results imply that the vaccine might alter disease expression in NOD mice by altering cellular immune function, such as by inducing a regulatory T cell population, altering the activity of antigen-presenting cells, or promoting the release of immunosuppressive cytokines (e.g. IL-4. TGF β)

REFERENCES

1. Yoon, J. W. Insulin-dependent diabetes mellitus. In Encyclopedia of Immunology, Second Edition (eds. I. M. Roitt & P. J. Delves). 1390–1398(London, UK: Academic Press Ltd., 1998).
2. Bath, J. F. Insulin-dependent diabetes mellitus as an autoimmune disease. Endocrine Reviews 15, 516–542 (1994).
3. Atkinson, M. A. & Maclaren N. K. Islet cell autoantigens in insulin-dependent diabetes. J. Clin. Invest. 92, 240–248 (1993).
4. Baekkeskov, S., et al. Identification of the 64K autoantigen in insulin-dependent diabetes as as the esizing glutamic acid decarboxylase. Nature 347,151–156(1990).
5. De Aizpura, H. J., Wilson, Y. M. & Harrison, L. C. Glutamic acid decarboxylase autoantibodies in preclinical insulin-dependent diabetes. Proc. Natl. Acad. Sci. USA 89, 9841–9845(1992).
6. Tian, J. et al. Modulating autoimmune response to GAD inhibits disease progression and prolongs graft survival in diabetes-prone mice. Nature Med. 2,1348–1353(1996).
7. Kaufman, D. L. et al. Spontaneous loss of T-cell tolerance to glutamic acid decarboxylase in murine insulin-dependent diabetes. Nature 366, 69–72 (1993).
8. Tisch, R. et al. Immune response to glutamic acid decarboxylase correlates with insulitis in non-obese diabetic mice. Nature 366, 72–75 (1993).
9. Yoon, J. W. et al. Control of autoimmune diabetes in NOD mice by expression or suppression of GAD in β cells. Science 284,1183–1187(1999).
10. Fenner, F. Risks and benefits of vaccinia virus use in the worldwide smallpox eradication campaign. Res. Virol. 140, 465–466(1989).
11. Henderson, D. A. & Arita, I. Utilization of vaccine in the global eradication of smallpox. In −1Xcinia Viruses as Vectors for Vaccine Antigens (ed. G. V. Quinnan, Jr.) 61–67(Elsevier, New York, 1985)
12. Moss, R. Genetically engineered poxviruses for recombinant gene expression, vaccination, and safety. Proc. Natl. Acad. Sci. USA 93, 11341–11348(1996)
13. Paoletti, E. Applications of pox virus vectors to vaccination. An update. Proc. Natl. Acad. Sci. USA 93,11349–11353(1996).
14. Brown, F., Schild, G. C. & Ada, G. L. Recombinant vaccinia viruses as vaccines. Nature 319, 549–550(1986).
15. Moss, B. V. vaccinia virus: a tool for research and vaccine development. Science 252,1662–1667(1991).
16. Hany, M., et al. Anti-viral protection and prevention of lymphocytic choriomeningitis or of the local footpad swelling reaction in mice immunization with vaccinia recombinant virus expressing LCMV-VVE nucleoprotein or glycoprotein. Eur. J. Immunol. 19, 417–424(1989).
17. Kulkarni, A. B., et al. Cytotoxic T cells specific for a single peptide on the M2 protein of respiratory syncytial virus are the sple mediators of resistance induced by immunization with M2 encoded by a recombinant vaccinia virus. J. Virol. 69,1261–1264(1995).
18. Cooney, E. L. et al., Enhanced immunity to human immunodeficiency virus(HIV) envelope elicited by a combined vaccine regimen, consisting of priming with a vaccine recombinant expressing HIV envelope and boosting with gp/60 protein. Proc. Natl. Acad. Sci. USA 90,1882–1886(1993).
19. Cooney, E. L., et al. Safety of and immunological response to a recombinant vaccinia virus vaccine expressing HIV envelope glycoprotein. Lancet 337, 569–572 (1991).
20. Lee, D. S., Tian, J., Phan, T. & Kaufman, D. L. Cloning and sequence analysis of murine cDNA encoding glutamic acid decarboxylase(GAD65). Biochem. Biophys. Acta 1216,157–160(1993).
21. Earl, P. L. & Moss B. Generation of recombinant vaccinia virus. In: Current Protocols in Molecular Biology (ed. F. M. Ausuble, et al.). 16.17.1–16.17.16 (Greene Publishing Associates, Wiley Interscience: New York, 1991).
22. Elliot, J. F. et al. Immuniztion with the larger isoform mouse glutamic acid decarboxylase (GAD67) prevents autoimmune diabetes in NOD mice. Diabetes 43,1494–1499(1994).
23. Ma, S. W. et al. Transgenic plants expressing autoantigens fed to mice to induce oral immune tolerance. Nature Med. 3, 793–796(1997).
24. Jun, H. S., Yoon, C. S., Zbytnuik, L., van Rooijen, N. & Yoon, J. W. Role of macrophages in T cell-mediated autoimmune diabetes in monobese diabeic mice. J. Exp. Med. 189, 347–358,1999.

In this disclosure, there is shown and described only the preferred examples of the invention, but, as aforementioned, it is to be understood that the invention is capable of use in various other combinations and environments and is capable of changes or modifications within the scope of the inventive concepts as expressed herein.

What is claimed is:

1. A method for delaying onset of type 1 diabetes mellitus comprising:

administering a vaccine comprising a recombinant vaccinia virus incorporated with a gene for coding glutamic acid decarboxylase.

2. The method of claim 1 wherein an effective amount of the vaccine is in the range of $1 \times 10^3 \sim 1 \times 10^{11}$ PFU.

* * * * *